United States Patent [19]

Carini et al.

[11] Patent Number: 4,632,930
[45] Date of Patent: Dec. 30, 1986

[54] ANTIHYPERTENSIVE ALKYL-ARYLIMIDAZOLE, THIAZOLE AND OXAZOLE DERIVATIVES

[75] Inventors: David J. Carini; Ruth R. Wexler, both of Wilmington, Del.

[73] Assignee: E. I. Du Pont de Nemours and Company, Wilmington, Del.

[21] Appl. No.: 676,938

[22] Filed: Nov. 30, 1984

[51] Int. Cl.⁴ .................. A61K 31/425; A61K 31/42; A61K 31/415; C07D 277/28; C07D 277/26; C07D 277/24; C07D 277/22; C07D 263/32; C07D 233/64

[52] U.S. Cl. .................................. 514/365; 514/374; 514/400; 514/929; 548/203; 548/204; 548/205; 548/235; 548/236; 548/342

[58] Field of Search ............... 548/342, 235, 236, 203, 548/204, 205; 514/374, 385, 400, 365

[56] References Cited

U.S. PATENT DOCUMENTS

| | | | |
|---|---|---|---|
| 3,888,870 | 6/1975 | Jackson | 548/186 |
| 4,001,420 | 1/1977 | Malen et al. | 514/365 |
| 4,020,082 | 4/1977 | Marchetti | 548/235 |
| 4,190,666 | 2/1980 | Cherkofsky | 514/398 |
| 4,348,404 | 9/1982 | Whitney | 548/342 |
| 4,372,964 | 2/1983 | Whitney | 514/400 |
| 4,451,471 | 5/1984 | Ferrini et al. | 546/270 |
| 4,472,422 | 9/1984 | Whitney | 514/341 |
| 4,576,958 | 3/1986 | Wexler | 514/400 |

FOREIGN PATENT DOCUMENTS 0092239 10/1983 European Pat. Off. .

Primary Examiner—Donald G. Daus
Assistant Examiner—Stephen M. Kapner

[57] ABSTRACT

Antihypertensive alkyl-arylheterocycle methanol or methanamine derivatives are useful in the treatment of hypertension.

45 Claims, No Drawings

ANTIHYPERTENSIVE ALKYL-ARYLIMIDAZOLE, THIAZOLE AND OXAZOLE DERIVATIVES

BACKGROUND OF THE INVENTION

This invention relates to alkyl-arylimidazole, thiazole and oxazole derivatives, pharmaceutical compositions containing them and methods of using them to treat hypertension.

Copending U.S. Patent Application No. 573214 filed Jan. 23, 1984, now U.S. Pat. No. 4,576,958 discloses antihypertensive 4,5-diarylimidazole methanol derivatives of the formula:

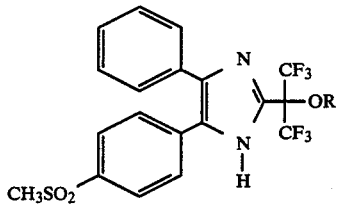

where R is H or

U.S. Pat. No. 4,472,422 issued to J. G. Whitney on Sept. 18, 1984 discloses antihypertensive 4,5-diarylimidazole methanamine derivatives of the formula:

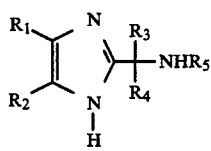

where $R_1$ and $R_2$ are aryl; $R_3$ and $R_4$ are halogenated alkyl; and $R_5$ is H, alkyl or

alkyl.

T. E. Jackson, U.S. Pat. No. 3,888,870, issued June 10, 1975, includes disclosure of thiazoles of the formula:

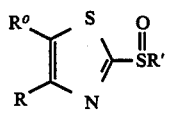

where R°, and R are independently hydrogen, lower alkyl or phenyl (unsubstituted or substituted), and $R^1$ is alkyl. The compounds are stated to have CNS depressant activity, (e.g. tranquilizer agents).

U.S. Pat. No. 4,451,471 issued to P. G. Ferrini and R. Goschke on May 29, 1984 discloses pharmaceutical compositions and antiinflammatory method of use of 2,4,5 trisubstituted thiazoles of the formula:

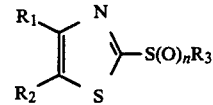

where $R_1$ and $R_2$ can be aryl or heteroaryl (unsubstituted or substituted), $R_3$ represents an aliphatic group unsubstituted or substituted by etherified or esterified hydroxy and n is an integer of 0–2.

U.S. Pat. No. 4,001,420 issued to C. Malen and P. Desnoyers on Apr. 25, 1974 discloses thiazoyl benzoic acid compounds possessing fibrinolytic and antiulcer properties of the formula:

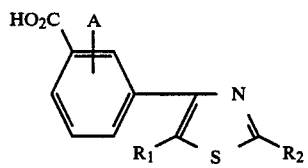

where $R_1$ and $R_2$ include lower alkyl, phenylalkyl or (substituted) phenyl and A can be hydrogen, halogen, or lower alkoxy.

European Pat. No. 92239, issued to K. Meguro and T. Fujita on Oct. 26, 1983, includes disclosure of oxazoles of the formula:

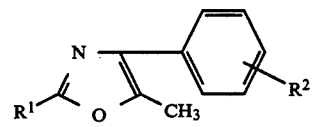

where $R^1$ is a hydrogen or a straight, branched or cyclic alkyl group of 1–6 carbon atoms, and where $R^2$ can be amongst other straight, branched or cyclic alkylthio of 1–3 carbon atoms. These compounds are of value as antidiabetic drugs.

Numerous antihypertensive agents are known in the art. There is nevertheless a continuing need for additional antihypertensive agents because of the various side effects which can occur with existing agents.

SUMMARY OF INVENTION

According to the present invention there is provided a compound having the formula:

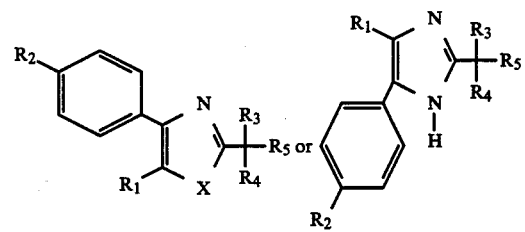

(I)  (Ia)

wherein

X is NH, S or O;

$R_1$ is a straight or branched chain alkyl of 1–7 carbon atoms, a straight or branched chain alkylene or alkyne of 2–7 carbon atoms, said alkyl, alkylene or alkyne optionally mono-, di- or tri-substituted with F, Cl or Br, cycloalkyl, cycloalkenyl, or cycloalkylalkyl of 3-7 carbon atoms,

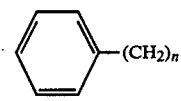

where n is 1 or 2, or

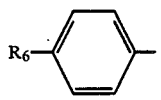

where $R_6$ is H, F, Cl or Br, with the proviso that when $R_1$ is

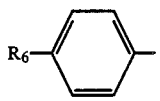

then X is S;

$R_2$ is $C_1-C_2$ alkyl $S(O)_m$ where m is 0, 1 or 2, $C_1-C_2$ alkoxy, cyano, acetyl or $NO_2$;

$R_3$ and $R_4$ independently are $CF_3$, $CF_2H$, $CF_2Cl$, $CFCl_2$, $CF_3CF_2$ or $CF_3CF_2CF_2$;

$R_5$ is $OR_7$ or $NHR_7$ where $R_7$ is H, alkyl of 1-3 carbon atoms, or

where $R_8$ is alkyl of 1-3 carbon atoms, phenyl or phenyl monosubstituted with F, Cl, Br, $NO_2$, $CF_3$, $C_1-C_2$ alkyl, or $C_1-C_2$ alkoxy, with the proviso that when $R_5$ is $NHR_7$ then X is NH; or a pharmaceutically suitable salt thereof.

Compounds of formulae (I) or (Ia) preferred for use for their antihypertensive activity are those compounds defined above except $R_1$ is not

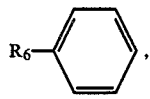

and $R_5$ is not $NHR_7$. Especially preferred are those compounds of formulae (I) or (Ia) wherein;

(a) $R_1$ is alkyl of 1-4 carbon atoms or

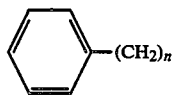

where n is 1 or 2; or (b) $R_2$ is $C_1-C_2$ alkyl $S(O)_m$ where m is 0, 1 or 2; or
(c) $R_3$ and $R_4$ are $CF_3$; or
(d) $R_5$ is OH.

Specifically preferred compounds are:
(a)    4-(1-methylethyl)-5-(4-methylsulfonylphenyl)-α,α-bis(trifluoromethyl)imidazole-2-methanol.
(b)    4-ethyl-5-(4-methylsulfonylphenyl)-α,α-bis(trifluoromethyl)imidazole-2-methanol.
(c)    4-(phenylmethyl)-5-(4-methylsulfonylphenyl)-α,α-bis(trifluoromethyl)imidazole-2-methanol.
(d)    4-cyclopentyl-5-(4-methylsulfonylphenyl)-α,α-bis(trifluoromethyl)imidazole-2-methanol.
(e)    4-cyclohexyl-5-(4-methylsulfonylphenyl)-α,α-bis(trifluoromethyl)imidazole-2-methanol.
(f)    5-(1-methylethyl)-4-(4-methylsulfonylphenyl)-α,α-bis(trifluoromethyl)thiazole-2-methanol.
(g)    5-ethyl-4-(4-methylsulfonylphenyl)-α,α-bis(trifluoromethyl)thiazole-2-methanol.
(h)    5-ethyl-4-(4-methylsulfonylphenyl)-α,α-bis(trifluoromethyl)oxazole-2-methanol.

SYNTHESIS

Compounds of Formulae (I) or (Ia) can be prepared via alkylation of the requisite disubstituted heterocycle.

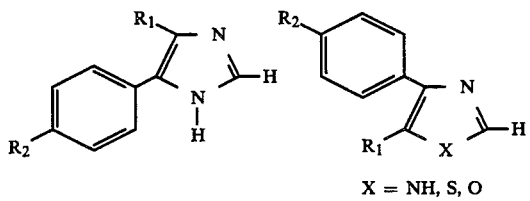

X = NH, S, O

The 4(5)alkyl-5(4)arylimidazoles are prepared as described in Brederick, H. et. al., *Chem. Ber.*, 86, 88 (1953), i.e., the appropriate α-haloketone is refluxed in formamide to give the corresponding 4,5-disubstituted imidazole unsubstituted at the 2-position.

The 5-alkyl-4 arylthiazoles can be prepared by the method described by Kurkjy, R. P. and Brown, E. V., *J. Am. Chem. Soc.*, 74, 5778 (1952). That is, thioformamide is generated in situ in an inert solvent such as dioxane and is reacted with the appropriate α-haloketone to give a thiazole unsubstituted at the 2-position.

The 5-alkyl-4-aryloxazoles can be prepared as described in Brederick, H. and Gompper, R. *Chem. Ber.*, 87, 700 (1954). That is, the appropriate α-haloketone is refluxed in a mixture of ammonium formate and formic acid to give the corresponding oxazole unsubstituted at the 2-position.

Compounds of Formulae (I) or (Ia), where X=NH, and $R_5$=OH can be prepared by contacting an N-protected 4(5)alkyl-5(4)arylimidazole with a strong base, such as n-butyl lithium, in an inert solvent at low temperature, followed by reaction with a fluorinated ketone. The nature of the N-protecting group is such that it is stable to strong base, but easily removed by acidic reagents. Examples of useful protecting groups are 2-tetrahydropyranyl, benzyloxymethyl, methoxymethyl, α-ethyoxyethyl, and β-methoxy-ethoxyethyl.

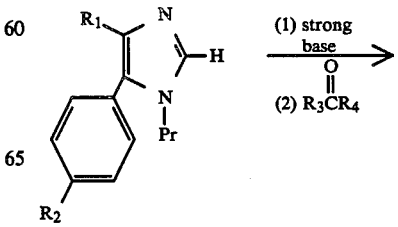

-continued

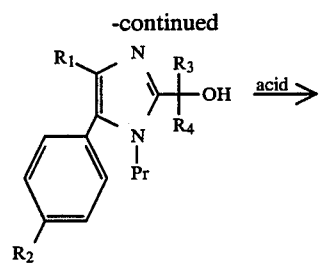

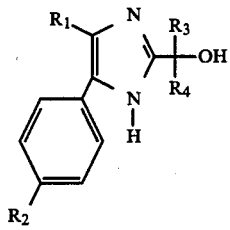

(Pr = Protecting Group)

The synthesis of N-protected 4,5-disubstituted imidazoles is described in U.S. Pat. No. 4,190,666; U.S. Pat. No. 4,182,769; and U.S. Pat. No. 4,159,338.

Compounds of Formula (I) where X=S or O, and $R_5$=OH can similarly be prepared, however the protecting group step is unnecessary.

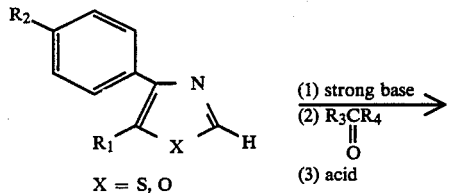

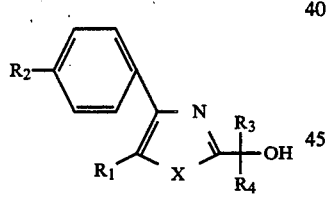

Compounds of Formulae (I) or (Ia) where X=NH and $R_5$=NH$_2$ can be prepared from the N-protected 4(5)-alkyl-5(4)arylimidazole by alkylation with an appropriate fluorinated ketone imine. Introduction of a fluorinated ketone imine where $R_5$=NH$_2$, requires the protection of the imine nitrogen with a group which can later be removed by acid. An example of a useful group is trimethylsilyl.

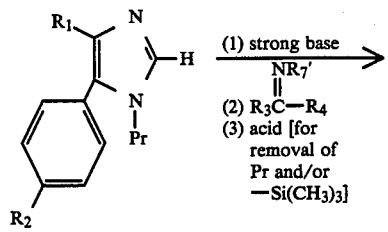

-continued

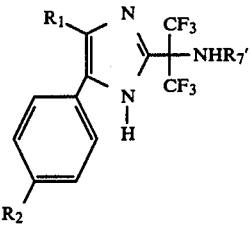

$R_7' = C_1$–$C_3$ alkyl or Si(CH$_3$)$_3$

Compounds of Formulae (I) and (Ia) of this invention with $R_2$=(C$_1$–C$_2$ alkyl)S(O)$_m$ can be prepared via oxidation of the corresponding sulfide to either the sulfoxide or sulfone. An oxidizing agent such as m-chloroperoxybenzoic acid (MCPBA) at low temperatures in an inert solvent such as methylene chloride affords only the sulfoxide. Whereas, oxidation of the sulfide to the sulfone can be accomplished using potassium hydrogen persulfate (KHSO$_5$, commercially sold as oxone ®) in a suitable solvent such as methanol as described by B. M. Trost and D. P. Curran, *Tetrahedron Letters*, 22, 1287 (1981). The oxidation is best carried out as the last step of the synthesis.

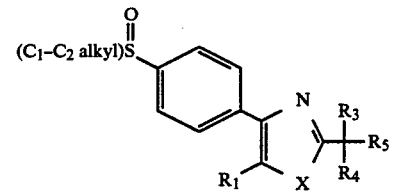

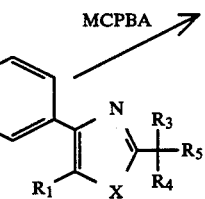

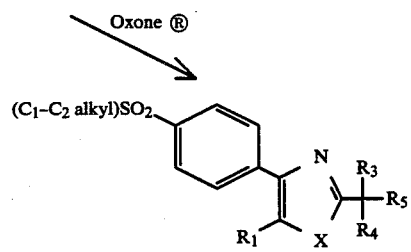

X = NH, S, O

The nitro group can be introduced at $R_2$ when X=NH by forming the nitrate salt of 4(5)alkyl-5(4)-phenylimidazole properly substituted at the 2-position, followed by refluxing the salt in sulfuric acid. The nitro group can be introduced at $R_2$ when X=S or O, via aromatic nitration of the corresponding thiazole or oxazole.

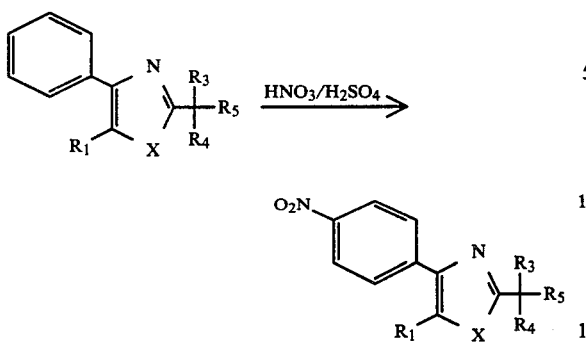

Compounds of Formulae (I) and (Ia) with $R_2=CN$ can be prepared from the corresponding 4(5)-p-bromophenylheterocycle derivative, (easily prepared by the Brederick procedure described above) by reaction with cyanide. This reaction can be carried out using copper cyanide in an inert solvent such as dimethylformamide at the reflux temperature. Conversion to the acetyl derivative can be accomplished via a Grignard reaction followed by hydrolysis. The Grignard reaction can be conducted using methyl magnesium halide in an ether solvent such as diethyl ether or tetrahydrofuran.

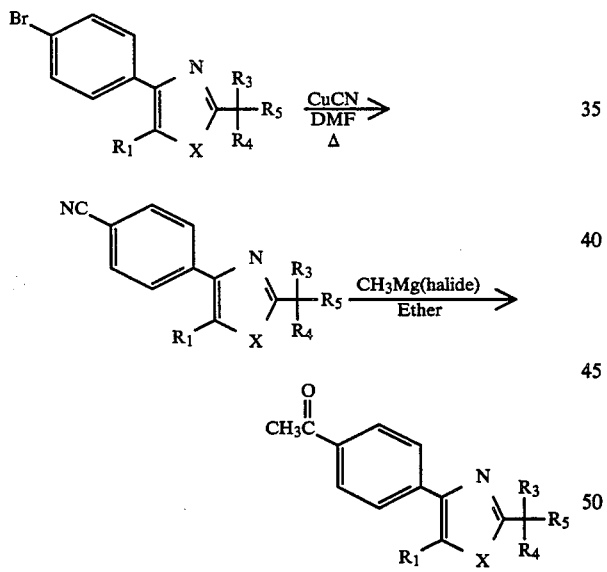

Compounds of Formulae (I) and (Ia) with $R_7=(C_1-C_3)$alkyl can be prepared from the N-protected imidazoles where $R_5=NH_2$ or OH, or the corresponding thiazoles or oxazoles by direct alkylation with $R_7L$ where L is any appropriate leaving group such as halide, toluenesulfonyloxy, or methanesulfonyloxy, followed by removal of the protecting group with acid when applicable. These alkylations can be conducted in the presence of a base, such as potassium carbonate, n-butyl lithium, triethylamine, potassium t-butoxide, sodium hydride or the like, in an inert solvent such as tetrahydrofuran, dimethylformamide or the like.

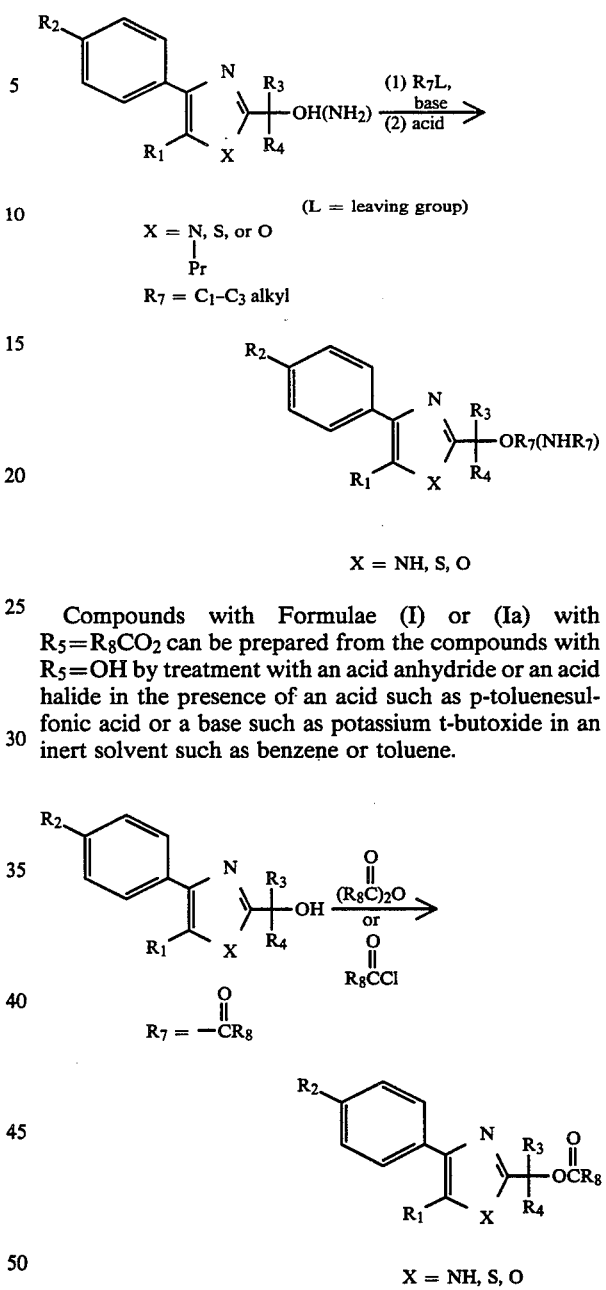

Compounds with Formulae (I) or (Ia) with $R_5=R_8CO_2$ can be prepared from the compounds with $R_5=OH$ by treatment with an acid anhydride or an acid halide in the presence of an acid such as p-toluenesulfonic acid or a base such as potassium t-butoxide in an inert solvent such as benzene or toluene.

The preparation of these compounds is further illustrated by the following examples. All parts are by weight unless otherwise specified.

EXAMPLE 1

4(1-methylethyl)-5-(4-methylthiophenyl)-α,α-bis(trifluoromethyl)-1H-imidazole-2-methanol Part (A)

3-Methyl-1-(4-methylthiophenyl)butanone

To a solution of 60.0 ml (0.49 mole) of isovalerylchloride in 600 ml of dry methylene chloride was added 29.03 ml (0.49 mole) of thioanisole. The solution was cooled to 5° C. in an ice-acetone bath, and anhydrous aluminum chloride (68.9 g, 0.52 mole) was added portionwise at a rate to maintain the temperature constant at 5° C. The reaction mixture was stirred at 5° C. for 3 hours, after which time the mixture was cautiously poured into 1050 ml of aqueous 1N HCl and was stirred overnight. The layers were separated and the aqueous was reextracted with methylene chloride (2×500 ml). The organic fractions were combined and washed with 1N hydrochloric acid (2×200 ml), 5% aqueous sodium hydroxide (2×200 ml) and brine (2×200 ml). The organic layer was dried over anhydrous magnesium sulfate and concentrated. The product was collected by filtration and washed with hexane to afford 84.5 g (82.5%) of 3-methyl-1-(4-methylthiophenyl)butanone as a white solid, m.p. 53°–55° C.

NMR (200 MHz, DMSO-d$_6$) δ 0.9 (s, 3H), 0.93 (s, 3H), 2.0–2.23 (m, 1H), 2.5 (s, 3H), 2.83 d, J=6.7 Hz, 2H), 7.33, 7.9 (AB, J$_{AB}$=7 Hz, 4H).

Part (B)

2-Bromo-3-methyl-1-(4-methylthiophenyl)butanone

To a suspension of 80 g (0.39 mole) of 3-methyl-1-(4-methylthiophenyl)butanone in 1400 ml of ether and 135 ml of methylene chloride was added dropwise a solution of 66.25 g (0.41 mole) of bromine in 200 ml of methylene chloride. The reaction mixture decolorized and became slightly exothermic. After stirring an additional 15 minutes, the mixture was concentrated in vacuo. The solid was collected by filtration and washed with hexane to give 104.7 g (95%) of 2-bromo-3-methyl-1-(4-methylthiophenyl)butanone as a white solid, m.p. 104°–106° C.

NMR (200 MHz, CDCl$_3$) δ 1.0 (d, 3H), 1.2 (d, 3H), 2.33–2.5 (m, 1H), 2.53 (s, 3H), 4.87 (d, 1H), 7.27, 7.92 (AB, J$_{AB}$=7 Hz, 4H).

Part (C)

4-(1-Methylethyl)-5-(4-methylthiophenyl)-1H-imidazole

A mixture of 35 g of 2-bromo-3-methyl-1-(4-methylmethylthiophenyl)butanone and 195 ml of formamide was refluxed under a dry air condenser for 2.5 hours. The reaction was cooled to 100° C. and 215 ml of water was added. The reaction mixture was cooled to 0° C., and the product was filtered off and washed with hexane. The solid was dried in a vacuum oven (75° C.) and then recrystallized to afford 11.93 g (42%) of the title compound as a tan solid, m.p. 206°–208° C.

NMR (200 MHz, DMSO-d$_6$) δ 1.23 (s, 3H), 1.27 (s, 3H), 2.5 (bs, 4H), 3.10–3.33 (m, 1H), 7.28, 7.47 (AB, J$_{AB}$=6.7 Hz, 4H), 7.67 (s, 1H).

Part (D)

4-(1-Methylethyl)-5-(4-methylthiophenyl)-1-(α-ethoxyethyl)imidazole

A mixture of 7.48 g (32.2 mmoles) of 4-(1-methylethyl)-5-(4-methythiophenyl)-1H-imidazole, 4.56 g (35.3 mmoles) of dichloroacetic acid and 17.57 g (0.24 mole) of ethyl vinyl ether in 350 ml of toluene were heated at reflux for 3.5 hours. The reaction mixture was cooled to room temperature and was then stirred overnight with 100 ml of 25% aqueous sodium hydroxide. The organic layer was separated and the aqueous was extracted with ether (2×). The organic fractions were combined, washed with brine, and dried over anhydrous potassium carbonate. Removal of the solvent in vacuo afforded 9.8 g of an orange oil which was used in the subsequent reaction without purification.

NMR (200 MHz, CDCl$_3$) δ 1.0–1.33 (m, 9H), 1.5 (d, J=5.5 Hz, 3H), 2.5 (s, 3H), 2.67–2.9 (m, 1H), 3.1–3.33 (m, 2H), 5.0–5.17 (m, 1H), 7.13, 7.3 (AB, J=6.7 Hz, 4H), 7.7 (s, 1H).

Part (E)

4-(1-Methylethyl)-5-(4-methylthiophenyl)α,α-bis(trifluoromethyl)-1H-imidazole-2-methanol To a stirred solution of 4-(1-methyethyl)-5-(4-methylthiophenyl)-1-(α-ethoxyethyl)imidazole (9.8 g, 32.2 mmol) in 110 ml of dry tetrahydrofuran was added 4.31 g (37.1 mmoles) of tetramethylethylenediamine. The reaction mixture was cooled to −78° C. and 32.24 ml of 1.65M n-butyl lithium in hexane was added dropwise via an addition funnel. After stirring the mixture an additional 20 minutes, hexafluoroacetone (9.0 ml) was condensed and added dropwise. The mixture was stirred at −78° C. for 1 hour and then 150 ml of saturated aqueous sodium bicarbonate solution was added dropwise. The reaction mixture was warmed to room temperature and the organic layer was separated. The aqueous layer was extracted with ethyl acetate. The organic layers were combined and concentrated to dryness in vacuo. The residue was stirred overnight in 215 ml of ethanol and 215 ml of 2N aqueous hydrochloric acid. The ethanol was removed in vacuo and the reaction mixture was basified to a pH of 8 with saturated aqueous potassium carbonate. The reaction mixture was extracted with ether, washed with 10% aqueous sodium bicarbonate and dried over anhydrous potassium carbonate. The residue was purified via flash chromatography on silica gel (92:8 hexane/ethyl acetate) to afford 7.55 g (59%) of a yellow oil which was triturated with hexane to give 7.55 g (59%) of the product as a white crystalline solid, m.p. 115°–117° C.

NMR (200 MHz, CDCl$_3$) δ 1.1–1.5 (m, 6H), 2.5 (s, 3H), 3.0–3.5 (m, 1H), 7.20–7.40 (m, 4H), 7.5 (s, 1H), 8.6–9.1 (bs, 1H).

EXAMPLE 2

4-(1-Methylethyl)-5-(4-methylsulfonylphenyl)-α,αbis(trifluoromethyl)-1H-imidazole-2-methanol A mixture of 4.0 g (0.01 mole) of 4-(1-methylethyl)-5-(4-methylthiophenyl)-α,α-bis(trifluoromethyl)-1H-imidazole-2-methanol, 16.06 g (0.026 mole) of Oxone ® (potassium hydrogen persulfate) and 115 ml of methanol was stirred at room temperature overnight. The inorganic solid was filtered off, and the filtrate was evaporated. The residue was partitioned between ethyl acetate and water. The layers were separated and the organic layer was washed with water, brine, dried over anhydrous magnesium sulfate and concentrated in vacuo. The product was recrystallized from dichloroethane affording 3.33 g (77%) of the title compound as a white solid, m.p. 182°–184° C.

NMR (200 MHz, DMSO-d$_6$) δ 1.36 (s, 3H), 1.42 (s, 3H), 3.16–3.43 (s, 3H, m, 1H), 7.77, 7.79 (AB, J$_{AB}$=6.7 Hz, 4H), 9.1 (s, 1H), 12.6–12.77 (bs, 1H).

EXAMPLE 3

4-(1-Methylethyl)-5-(4-methylthiophenyl)-α,α-bis(trifluoromethyl)-1H-imidazole-2-methanamine To a stirred solution of 4-(1-methylethyl)-5-(4-methylthiophenyl)-1-(α-ethoxyethyl)imidazole (12.0 g, 0.04 mole) in 150 ml of dry tetrahydrofuran was added 6.85 ml of tetramethylethylenediamine (0.045 moles).

The reaction was cooled to −78° C. and 39.47 ml of 1.6M n-butyl lithium in hexane was added dropwise. After stirring the mixture for 20 minutes, 15.45 g of [1,1-di(trifluoromethyl)methyleneamino]-trimethylsilane was added dropwise. The reaction mixture was stirred an additional hour, warmed to 0° C. and 140 ml of saturated aqueous sodium bicarbonate solution was added dropwise. The reaction was warmed to room temperature and the layers were separated. The aqueous layer was extracted with ethyl acetate. The organic layers were combined and concentrated and the residue was stirred overnight in 260 ml of ethanol and 260 ml of 2N aqueous hydrochloric acid. The ethanol was evaporated and the aqueous was extracted with ether (3×), dried over anhydrous magnesium sulfate, filtered and concentrated in vacuo. The product was purified by flash chromatography on silica gel (92:8 hexane/ethyl acetate) to afford 2.67 g of a white crystalline solid, m.p. 105°–107° C.

NMR (200 MHz, CDCl$_3$) δ 1.3 (s, 3H), 1.33 (s, 3H), 2.63–2.9 (m, 2H), 3.0–3.5 (m, 1H), 7.3, 7.57 (AB, J$_{AB}$=7 Hz, 4H), 8.83–9.1 (bs, 1H).

EXAMPLE 4

4-(1-Methylethyl)-5-(4-methylsulfonylphenyl)-α,α-bis(trifluoromethyl)-1H-imidazole-2-methanamine A mixture of 1.8 g (4.5 mmoles) of 4-(1-methylethyl)-5-(4-methylthiophenyl)-α,α-bis(trifluoromethyl)-1H-imidazole-2-methanamine, 7.25 g (11.8 mmoles) of Oxone ® (potassium hydrogen persulfate) and 50 ml of methanol were stirred together overnight. The solid was filtered off and the filtrate was evaporated in vacuo. The residue was partitioned between ethyl acetate and water and the layers were separated. The organic layer was washed with water and brine, dried over anhydrous magnesium sulfate and concentrated in vacuo to afford 2.1 g of an oil. The product was purified via flash chromatography on silica gel (73:27 hexane/ethyl acetate) to afford 1.02 g (53%) of the title compound as an off-white crystalline solid, m.p. 155°–157° C.

NMR (200 MHz, CDCl$_3$) δ 1.33 (s, 3H), 1.36 (s, 3H), 2.73 (s, 2H), 3.03 (s, 3H), 3.26–3.50 (m, 1H), 7.86, 7.97 (AB, J$_{AB}$=6.7 Hz, 4H), 9.13–9.4 (bs, 1H).

EXAMPLE 5

4-(1-Methylethyl)-5-(4-nitrophenyl)-α,α-bis(trifluoromethyl)-1H-imidazole-2-methanol Part (A)

4-(1-Methylethyl)-5-phenyl-1-(α-ethoxyethyl)imidazole

A mixture of 10.0 g (0.055 mole) of 4-(1-methylethyl)-5-phenyl-1H-imidazole, 7.61 g (0.06 mole) of dichloroacetic acid and 29.3 g (0.41 mole) of ethyl vinyl ether in 585 ml of toluene was heated at reflux for 3.5 hours. The reaction mixture was cooled to room temperature and was then stirred overnight with 170 ml of 25% aqueous sodium hydroxide. The organic layer was separated. The aqueous was extracted with ether (2×). The organic fractions were combined, washed with brine and dried over anhydrous potassium carbonate. Removal of the solvent under vacuum afforded 13.8 g of an oil, which was used in the subsequent reaction without purification.

NMR (200 MHz, CDCl$_3$) δ 1.0–1.33 (m, 9H), 1.5 (d, 3H), 2.67–2.83 (m, 1H), 3.0–3.5 (m, 2H), 5.1 (q, 1H), 7.0–7.5 (m, 5H), 7.7 (s, 1H).

Part (B)

4-(1-Methylethyl)-5-(phenyl)-α,α-bis(trifluoromethyl)-1H-imidazole-2-methanol

To a stirred solution of 4-(1-methylethyl)-5-phenyl-1-(α-ethoxyethyl)imidazole (13.9 g, 0.054 mole) in 210 ml of dry tetrahydrofuran was added 9.45 ml of tetramethylethylenediamine (0.06 moles). The reaction was cooled to −78° C. and 56.15 ml of 1.66M n-butyl lithium in hexane was added dropwise. After stirring the mixture for 20 minutes, hexafluoroacetone (14.0 ml) was condensed and added dropwise. The reaction was stirred an additional hour at −78° C. and then 275 ml of saturated aqueous sodium bicarbonate solution was added dropwise. After warming to room temperature, the layers were separated and the aqueous was extracted with ethyl acetate. The organic layers were combined and concentrated in vacuo. The residue was stirred overnight in 350 ml of ethanol and 350 ml of 2N aqueous hydrochloric acid. The ethanol was evaporated and the reaction mixture was basified to a pH of 8 with saturated aqueous potassium carbonate. The mixture was extracted with ether, washed with 10% aqueous sodium bicarbonate and dried over anhydrous magnesium sulfate. The residue was purified via flash chromatography on silica gel (98:2 hexane/ethyl acetate) to afford 13.19 g (70%) of the product which was recrystallized from hexane to give a white crystalline solid, m.p. 80°–81° C.

NMR (200 MHz, CDCl$_3$) δ 1.23–1.50 (m, 6H), 3.0–3.5 (m, 1H), 5.7–6.2 (bs, 1H), 7.2–7.7 (m, 5H), 8.73–9.1 (bs, 1H).

Part (C)

4-(1-methylethyl)-5-(4-nitrophenyl)-α,α-bis(trifluoromethyl)-1H-imidazole-2-methanol To a suspension of 4-(1-methylethyl)-5-phenyl-α,α-bis(trifluoromethyl)-1H-imidazole-2-methanol (1.75 g) in 40 ml of water was added 2.5 ml of concentrated nitric acid in a dropwise manner. The mixture was stirred for 30 minutes, and the nitrate salt, 1.51 g) was filtered off. The solid in 5 ml of concentrated sulfuric acid was heated at reflux for 2 hours. The reaction mixture was poured into 50 ml of ice-water. The mixture was basified to a pH of 8 and extracted with ethyl acetate. The organic layer was washed with brine, dried over anhydrous magnesium sulfate, filtered and concentrated to dryness to afford a yellow solid which was purified by flash chromatography on silica gel (85:15 hexane/ethyl acetate) to afford (0.98 g, 50%) of the title compound as a pale yellow solid, m.p. 157°–160° C.

NMR (200 MHz, CDCl$_3$) δ 1.37 (s, 3H), 1.4 (s, 3H), 3.33–3.6 (m, 1H), 5.50–5.76 (bs, 1H), 7.83, 8.3 (AB, J$_{AB}$=8 Hz, 4H), 9.0–9.27 (bs, 1H).

Following the procedures in Examples 1–5 and the general synthesis disclosure the following compounds were prepared or can be prepared:

TABLE 1

| Example | $R_1$ | $R_2$ | $R_3$ | $R_4$ | $R_5$ | m.p. °C. |
|---|---|---|---|---|---|---|
| 1 | i-$C_3H_7$ | $CH_3S$ | $CF_3$ | $CF_3$ | OH | 115–117 |
| 2 | i-$C_3H_7$ | $CH_3SO_2$ | $CF_3$ | $CF_3$ | OH | 182–184 |
| 3 | i-$C_3H_7$ | $CH_3S$ | $CF_3$ | $CF_3$ | $NH_2$ | 105–107 |
| 4 | i-$C_3H_7$ | $CH_3SO_2$ | $CF_3$ | $CF_3$ | $NH_2$ | 155–157 |
| 5 | i-$C_3H_7$ | $NO_2$ | $CF_3$ | $CF_3$ | OH | 157–160 |
| 6 | $CH_3$ | $CH_3SO_2$ | $CF_3$ | $CF_3$ | OH | 222–224 |
| 7 | $CH_3CH_2$ | $CH_3SO_2$ | $CF_3$ | $CF_3$ | OH | 175–177 |
| 8 | $CH_3CH_2$ | $CH_3S$ | $CF_3$ | $CF_3$ | OH | 102–105 |
| 9 | n-$C_5H_{11}$ | $CH_3SO_2$ | $CF_3$ | $CF_3$ | OH | 156–158 |
| 10 | cyclopentyl | $CH_3SO_2$ | $CF_3$ | $CF_3$ | OH | 203–204 |
| 11 | cyclohexyl | $CH_3SO_2$ | $CF_3$ | $CF_3$ | OH | 184–186 |
| 12 | t-butyl | $CH_3SO_2$ | $CF_3$ | $CF_3$ | OH | 193–195 |
| 13 | $PhCH_2$ | $CH_3SO_2$ | $CF_3$ | $CF_3$ | OH | 178–179.5 |
| 14 |  | $CH_3SO_2$ | $CF_3$ | $CF_3$ | OH |  |
| 15 | $CF_3CH_2$ | $CH_3SO_2$ | $CF_3$ | $CF_3$ | OH |  |
| 16 | cyclohexenyl | $CH_3SO_2$ | $CF_3$ | $CF_3$ | OH |  |
| 17 | n-$C_3H_7$ | $CH_3SO_2$ | $CF_3$ | $CF_3$ | OH |  |
| 18 | $CH_3CH_2$ | $CH_3CH_2SO_2$ | $CF_3$ | $CF_3$ | OH |  |
| 19 | $CH_3CH_2$ | $CH_3SO_2$ | $CF_3CF_2$ | $CF_3$ | OH |  |
| 20 | i-$C_3H_7$ | $CH_3SO_2$ | $CF_2Cl$ | $CF_3$ | OH |  |
| 21 | $PhCH_2$ | $CH_3SO_2$ | $CF_3$ | $CF_3$ | $NH_2$ |  |
| 22 | $CH_3CH_2$ | $NO_2$ | $CF_3$ | $CF_3$ | OH |  |
| 23 | $CH_2=CH_2-CH_2$ | $CH_3SO_2$ | $CF_3$ | $CF_3$ | OH |  |
| 24 | $CH_3CH_2-$ | $CH_3CO$ | $CF_3$ | $CF_3$ | OH |  |
| 25 | n-$C_3H_7$ | CN | $CF_3$ | $CF_3$ | OH |  |
| 26 | i-$C_3H_7$ | $CH_3SO_2$ | $CF_3$ | $CF_3$ | $OCH_3$ |  |
| 27 | $CH_3CH_2$ | $CH_3SO_2$ | $CF_3$ | $CF_3$ | $OCOCH_3$ |  |
| 28 | $CH_3CH_2$ | $CH_3SO_2$ | $CF_3$ | $CF_3$ | OCOPh |  |

Ph = phenyl

EXAMPLE 29

5-(1-Methylethyl)-4-(4-methylthiophenyl)-α,α-bis(trifluoromethyl)thiazole-2-methanol

Part (A)

5-(1-Methylethyl)-4-(4-methylthiophenyl)thiazole

To a suspension of 3.57 g of phosphorus pentasulfide (8.03 mmol as $P_4S_{10}$) in 16 ml of 1,4-dioxane at 25° C. was added 3.13 ml of formamide (78.5 mmol). After a few minutes the mixture became exothermic and was placed in an ice-water bath to prevent refluxing of the solvent. Immediately, 16.0 g (49.8 mmol) of 2-bromo-3-methyl-1-(4-methylthiophenyl)butanone was added at a slow addition rate to maintain the mixture below the reflux temperature. Following this addition, the reaction mixture was refluxed for 1 hour. After which time, 10 ml of 2N hydrochloric acid was added and the resulting solution was refluxed for 1 hour, and then concentrated in vacuo. The residue was dissolved in dilute aqueous sodium hydroxide solution and was extracted with ethyl acetate. The combined organic phases were washed with water, saturated sodium bicarbonate solution, and brine. The solution was dried with magnesium sulfate, filtered, and concentrated. The crude product was purified by flash chromatography on silica gel (elution: 0–10% ethyl acetate/benzene) to provide 4.5 g of 5-(1-methylethyl)-4-(4-methylthiophenyl)thiazole as a yellow oil.

NMR (200 MHz, $CDCl_3$) δ 1.32 (d, 6H, J=6.6 Hz), 2.5 (s, 3H), 3.50 (sept, J=6.6 Hz, 1H), 7.44 (AB, $J_{AB}$=8.5 Hz, 4H), 8.70 (s, 1H).

Part (B)

5-(1-Methylethyl)-4-(4-methylthiophenyl)-α,α-bis(trifluoromethyl)thiazole-2-methanol To a solution of 4.50 g (18.0 mmol) of 5-(1-methylethyl)-4-(4-methylthiophenyl)thiazole and 3.15 ml (20.9 mmol) of tetramethylethylenediamine in 85 ml of tetrahydrofuran at −78° C. was added dropwise 20.0 ml (32.0 mmol) of n-butyl lithium (1.6M in hexane). The resulting solution was stirred for 1 hour at −78° C., and then 5.6 ml (50 mmol) of hexafluoroacetone was added dropwise. The mixture was stirred for 1 hour at −78° C. and then quenched by the rapid addition of 50 ml of sodium bicarbonate solution. After warming to 25° C., the organic and aqueous phases were separated and the aqueous phase was extracted with tetrahydrofuran. The combined organic phases were then washed with brine, dried over anhydrous potassium carbonate, filtered, and concentrated. The residue was dissolved in a mixture of 150 ml of ethanol and 30 ml of 4N hydrochloric acid; and the solution was stirred overnight at 25° C. The solution was concentrated in vacuo to remove the ethanol and the resulting aqueous mixture was extracted with diethyl ether. The combined organic phases were washed with brine, dried over anhydrous magnesium sulfate, filtered, and concentrated. The crude product was purified by flash chromatography on silica gel (elution-benzene) to provide 5.9 g of 5-(1-methylethyl)-4-(4-methylthiophenyl)-α,α-bis(trifluoromethyl)thiazole-2-methanol as a light orange oil.

NMR (200 MHz, CDCl$_3$) δ 1.37 (d, 6H, J=6.7 Hz), 2.53 (s, 3H), 3.49 (sept, J=6.7 Hz, 1H), 5.98 (s, 1H), 7.41 (AB, J$_{AB}$=8.3 Hz, 4H).

EXAMPLE 30

5-(1-Methylethyl)-4-(4-methylsulfonylphenyl)-α,α-bis(trifluoromethyl)thiazole-2-methanol To a solution of 5.90 g (14.2 mmol) of 5-(1-methylethyl)-4-(4-methylthiophenyl)-α,α-bis(trifluoromethyl)-thiazole-2-methanol in 200 ml of methanol at 25° C. was added 21.3 g (34.7 mmol) of Oxone ® (potassium hydrogen persulfate) and the resulting suspension was stirred at 25° C. for 3 hours. The suspension was filtered, and the filtrate concentrated in vacuo. The residue was dissolved in ethyl acetate; and the solution was washed with distilled water and brine, dried over anhydrous magnesium sulfate, filtered and concentrated. The crude product was recrystallized from n-butyl chloride to provide 3.34 g of 5-(1-methylethyl)-4-(4-methylsulfonylphenyl)-α,α-bis(trifluoromethyl)-thiazole-2-methanol as a yellow crystalline solid, m.p. 122°-123° C.

NMR (200 MHz, CDCl$_3$) δ 1.39 (d, J=6.4 Hz, 6H), 3.08 (s, 3H), 3.51 (sept, J=6.4 Hz, 1H), 5.82 (s, 1H), 7.93 (AB, J$_{AB}$=8.7 Hz, 4H).

Following the procedures given in Examples 29, 30 and the general synthesis disclosure, the following compounds were prepared or can be prepared:

TABLE 2

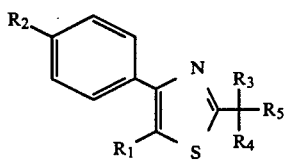

| Example | R$_1$ | R$_2$ | R$_3$ | R$_4$ | R$_5$ | m.p. °C. |
|---|---|---|---|---|---|---|
| 29 | i-C$_3$H$_7$ | CH$_3$S | CF$_3$ | CF$_3$ | OH | oil |
| 30 | i-C$_3$H$_7$ | CH$_3$SO$_2$ | CF$_3$ | CF$_3$ | OH | 122–123 |
| 31 | C$_6$H$_5$ | CH$_3$SO$_2$ | CF$_3$ | CF$_3$ | OH | 149–150 |
| 32 | CH$_3$CH$_2$ | CH$_3$SO$_2$ | CF$_3$ | CF$_3$ | OH | 120.5–122 |
| 33 | ⌁cyclopentyl | CH$_3$SO$_2$ | CF$_3$ | CF$_3$ | OH | 103–104.5 |
| 34 | PhCH$_2$ | CH$_3$SO$_2$ | CF$_3$ | CF$_3$ | OH | 188–189 |
| 35 | n-C$_5$H$_{11}$ | CH$_3$SO$_2$ | CF$_3$ | CF$_3$ | OH | |
| 36 | CF$_3$ | CH$_3$SO$_2$ | CF$_3$ | CF$_3$ | OH | |
| 37 | cyclohexyl | CH$_3$SO$_2$ | CF$_3$ | CF$_3$ | OH | |
| 38 | cyclopropyl | CH$_3$SO$_2$ | CF$_3$ | CF$_3$ | OH | |
| 39 | n-C$_3$H$_7$ | CH$_3$SO$_2$ | CF$_3$ | CF$_3$ | OH | |
| 40 | CH$_3$CH$_2$ | CH$_3$SO$_2$ | CF$_3$CF$_2$ | CF$_3$ | OH | |
| 41 | i-C$_3$H$_7$ | CH$_3$CH$_2$SO$_2$ | CF$_3$ | CF$_3$ | OH | |
| 42 | CH$_3$CH$_2$ | CH$_3$SO$_2$ | CF$_3$ | CF$_2$Cl | OH | |
| 43 | CH$_3$ | CH$_3$SO$_2$ | CF$_3$ | CF$_3$ | OCH$_3$ | |

EXAMPLE 44

5-Ethyl-4-(4-methylthiophenyl)-α,α-bis(trifluoromethyl)oxazole-2-methanol

Part (A)

5-Ethyl-4-(4-methylthiophenyl)oxazole

A solution of 20.0 g of 2-bromo-1-(4-methylthiophenyl)butanone (73.2 mmol) and 16.25 g of ammonium formate (258 mmol) in 80 ml of formic acid (95–97%) was heated to reflux for 6 hours. After cooling, the reaction mixture was diluted with water and then made basic with 50% aqueous sodium hydroxide solution. The resulting mixture was extracted with diethyl ether. The combined organic phases were washed with saturated sodium chloride solution, dried over anhydrous magnesium sulfate, filtered, and concentrated. The crude product was purified by flash chromatography on silica gel (elution: methylene chloride) to afford 2.50 g of 5-ethyl-4-(4-methylthiophenyl)oxazole as an orange oil.

NMR (200 MHz, CDCl$_3$) δ 1.30 (t, J=7.3 Hz, 3H) 1.51 (s, 3H), 2.8 (q, J=7.3 Hz, 2H), 7.43 (AB, 4H) and 7.78 (s, 1H).

Part (B)

5-Ethyl-4-(4-methylthiophenyl)-α,α-bis(trifluoromethyl)oxazole-2-methanol

To a solution of 2.50 g (11.4 mmol) of 5-ethyl-4-(4-methylthiophenyl)oxazole and 2.0 ml (13.3 mmol) of tetramethylethylenediamine in 50 ml of tetrahydrofuran at −78° C. was added dropwise 12.6 ml (20.2 mmol) of n-butyl lithium (1.6M in hexane). The resulting solution was stirred for 1 hour at −78° C., and then 3.5 ml (31 mmol) of hexafluoroacetone was added dropwise. The mixture was stirred for 1 hour at −78° C. and then quenched by the rapid addition of 30 ml of sodium bicarbonate solution. After warming to 25° C., the organic and aqueous phases were separated and the aqueous phase was extracted with tetrahydrofuran. The combined organic phases were then washed with brine, dried over anhydrous potassium carbonate, filtered, and concentrated. The residue was dissolved in a mixture of 100 ml of ethanol and 20 ml of 4N hydrochloric acid; and the solution was stirred overnight at 25° C. The solution was concentrated in vacuo to remove the ethanol and the resulting aqueous mixture was extracted with diethyl ether. The combined organic phases were washed with brine, dried over anhydrous magnesium sulfate, filtered, and concentrated. The crude product was purified by flash chromatography on silica gel (elution-benzene) to provide 3.28 g of 5-ethyl-4-(4-methylthiophenyl)-α,α-bis(trifluoromethyl)oxazole-2-methanol as a light orange oil.

NMR (200 MHz, CDCl$_3$) δ 1.33 (t, J=7.5 Hz, 3H) 1.52 (s, 3H), 2.95 (q, J=7.5 Hz, 2H), 4.98 (s, 1H) and 7.42 (AB, 4H).

EXAMPLE 45

5-Ethyl)-4-(4-methylsulfonylphenyl)-α,α-bis(trifluoromethyl)oxazole-2-methanol

To a solution of 3.28 g (8.5 mmol) of 5-ethyl-4-(4-methylthophenyl)-α,α-bis(trifluoromethyl)oxazole-2-methanol in 120 ml of methanol at 25° C. was added 12.8 g (20.9 mmol) of Oxone® monopersulfate compound (potassium peroxymonosulfate) and the resulting suspension was stirred at 25° C. for 3 hours. The suspension was filtered, and the filtrate concentrated in vacuo. The residue was dissolved in ethyl acetate; and the solution was washed with distilled water and brine, dried over anhydrous magnesium sulfate, filtered and concentrated. The crude product was recrystallized from n-butyl chloride to provide 2.3 g of 5-ethyl-4-(4-methylsulfonylphenyl)-α,α-bis(trifluoromethyl)oxazole-2-methanol as a white crystalline solid, m.p. 92°–93° C.

NMR (200 MHz, CDCl$_3$) δ 1.37 (t, J=7.3 Hz, 3H), 3.01 (q, J=7.3 Hz, 2H), 3.07 (s, 3H), 4.99 (s, 1H) and 7.91 (AB, 4H).

Following the procedures given in Examples 44 and 45 and the general synthesis disclosure, the following compounds were prepared or can be prepared.

TABLE 3

| Ex. | R$_1$ | R$_2$ | R$_3$ | R$_4$ | R$_5$ | m.p. (°C.) |
|---|---|---|---|---|---|---|
| 44 | CH$_3$CH$_2$ | CH$_3$S | CF$_3$ | CF$_3$ | OH | oil |
| 45 | CH$_3$CH$_2$ | CH$_3$SO$_2$ | CF$_3$ | CF$_3$ | OH | 92–93° C. |
| 46 | i-C$_3$H$_7$ | CH$_3$SO$_2$ | CF$_3$ | CF$_3$ | OH | |
| 47 | ⌬- | CH$_3$SO$_2$ | CF$_3$ | CF$_3$ | OH | |
| 48 | CF$_3$ | CH$_3$SO$_2$ | CF$_3$ | CF$_3$ | OH | |

TABLE 3-continued

| Ex. | R$_1$ | R$_2$ | R$_3$ | R$_4$ | R$_5$ | m.p. (°C.) |
|---|---|---|---|---|---|---|
| 49 | ▷- | CH$_3$SO$_2$ | CF$_3$ | CF$_3$ | OH | |
| 50 | n-C$_3$H$_7$ | CH$_3$SO$_2$ | CF$_3$ | CF$_3$ | OH | |
| 51 | CH$_3$CH$_2$ | CH$_3$SO$_2$ | CF$_3$ | CF$_3$ | OCOCH$_3$ | |
| 52 | CH$_3$CH$_2$ | NO$_2$ | cf$_3$ | CF$_3$ | OH | |
| 53 | ⌬- | CH$_3$SO$_2$ | CF$_3$ | CF$_3$ | OH | |

DOSAGE FORMS

The compounds of this invention can be administered in the treatment of hypertension according to the invention by any means that effects contact of the active ingredient compound with the site of action in the body of a warm-blooded animal. For example, administration can be parenteral, i.e., subcutaneous, intravenous, intramuscular, or intraperitoneal. Alternatively or concurrently, administration can be by the oral route.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.05 to 50 milligrams per kilogram of body weight. Ordinarily, from 0.1 to 40, and preferably 0.5 to 20, milligrams per kilogram per day in one or more applications per day is effective to obtain desired results. For the more potent compounds of the invention, e.g., 4-ethyl-5-(4-methylsulfonylphenyl)-α,α-bis(-trifluoromethyl)imidazole-2-methanol the daily dose ranges are from about 0.01 to 5 mg/kg, preferably 0.02 to 5 mg/kg, and more preferably 0.05 to 2 mg/kg.

Dosage forms (compositions) suitable for internal administration contain from about 0.1 milligrams to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms.

Gelatin capsules can contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidixing agents such as sodium bisulfite, sodium sulfite, or ascorbic acid either alone or combined are suitable stabilizing agents. Also used are citric acid and its salts and sodium EDTA. IN addition parenteral solutions can contain preservatives, such as benzalkonium chloride, methyl- or propyl-paraben, and chlorobutanol.

Suitable pharmaceutical carriers are described in *Remington's Pharmaceutical Sciences*, A. Osol, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 50 milligrams of powdered active ingredient, 175 milligrams of lactose, 24 milligrams of talc, and 6 milligrams magnesium stearate.

Soft Gelatin Capsules

A mixture of active ingredient in soybean oil is prepared and injected by means of a positive displacement pump into gelatin to form soft gelatin capsules containing 50 milligrams of the active ingredient. The capsules are washed and dried.

Tablets

A large number of tablets are prepared by conventional procedures so that the dosage unit is 50 milligrams of active ingredient, 6 milligrams of magnesium stearate, 70 milligrams of microcrystalline cellulose, 11 milligrams of cornstarch and 27.5 milligrams of lactose. Appropriate coatings may be applied to increase palatability or delay absorption.

Injectable

A parenteral composition suitable for administration by injection is prepared by stirring 1.5% by weight of active ingredient in 10%–60% by volume of co-solvents, like propylene glycol in water. The resultant solution can be sterilized by filtration.

Suspension

An aqueous suspension is prepared for oral administration so that each 5 milliliters contain 10 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

UTILITY

Rat Tests

The antihypertensive activity of the compounds of this invention is evidenced by tests conducted in spontaneously hypertensive rats (SHR). Graded dose levels of each compound are administered orally to groups of eight hypertensive rats. The compound is prepared in an aqueous 0.25% methylcellulose vehicle and administered at a volume to body weight ratio of 5.0 ml/kg. A group of hypertensive rats receiving the aqueous vehicle by the same route serve as controls for each test. At various intervals of time after treatment, usually 90 minutes, the systolic arterial blood pressure of each rat is determined by modification of the microphone-manometer technique (Friedman, M. and Freed, S. C., *Proc. Soc. Exp. Biol. and Med.*, 70, 670 (1949)). That dose of compound which produces a 30 mm mercury (mm Hg) reduction in blood pressure when compared to the mean systolic arterial blood pressure of the control animals is then determined (Effective Dose 30 = $ED_{30}$).

The compounds listed in Table 4 are effective in lowering blood pressure when doses orally in spontaneously hypertensive rats.

TABLE 4

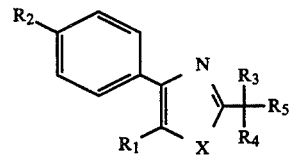

| Example | $R_1$ | $R_2$ | $R_3$ | $R_4$ | $R_5$ | X | SHR $ED_{30}$ (mg/kg, p.o.) |
|---|---|---|---|---|---|---|---|
| 1 | i-$C_3H_7$ | $CH_3S$ | $CF_3$ | $CF_3$ | OH | NH | 0.18 |
| 2 | i-$C_3H_7$ | $CH_3SO_2$ | $CF_3$ | $CF_3$ | OH | NH | 0.24 |
| 4 | i-$C_3H_7$ | $CH_3SO_2$ | $CF_3$ | $CF_3$ | $NH_2$ | NH | 1.8 |
| 5 | i-$C_3H_7$ | $NO_2$ | $CF_3$ | $CF_3$ | OH | NH | 2.3 |
| 6 | $CH_3$ | $CH_3SO_2$ | $CF_3$ | $CF_3$ | OH | NH | 2.4 |
| 7 | $CH_3CH_2$ | $CH_3SO_2$ | $CF_3$ | $CF_3$ | OH | NH | 0.1 |
| 8 | $CH_3CH_2$ | $CH_3S$ | $CF_3$ | $CF_3$ | OH | NH | 0.16 |
| 9 | n-$C_5H_{11}$ | $CH_3SO_2$ | $CF_3$ | $CF_3$ | OH | NH | 2.1 |
| 10 | cyclopentyl | $CH_3SO_2$ | $CF_3$ | $CF_3$ | OH | NH | 0.55 |
| 11 | cyclohexyl | $CH_3SO_2$ | $CF_3$ | $CF_3$ | OH | NH | 0.59 |
| 12 | t-butyl | $CH_3SO_2$ | $CF_3$ | $CF_3$ | OH | NH | 3.7 |
| 13 | $PhCH_2$ | $CH_3SO_2$ | $CF_3$ | $CF_3$ | OH | NH | 1.0 |
| 30 | i-$C_3H_7$ | $CH_3SO_2$ | $CF_3$ | $CF_3$ | OH | S | 0.33 |
| 31 | $C_6H_5$ | $CH_3SO_2$ | $CF_3$ | $CF_3$ | OH | S | 3.0 |
| 32 | $CH_3CH_2$ | $CH_3SO_2$ | $CF_3$ | $CF_3$ | OH | S | 0.28 |
| 33 | cyclopentyl | $CH_3SO_2$ | $CF_3$ | $CF_3$ | OH | S | 0.94 |
| 34 | $PhCH_2$ | $CH_3SO_2$ | $CF_3$ | $CF_3$ | OH | S | 27 |
| 45 | $CH_3CH_2$ | $CH_3SO_2$ | $CF_3$ | $CF_3$ | OH | O | 1.5 |

What is claimed is:

1. A compound having the formula:

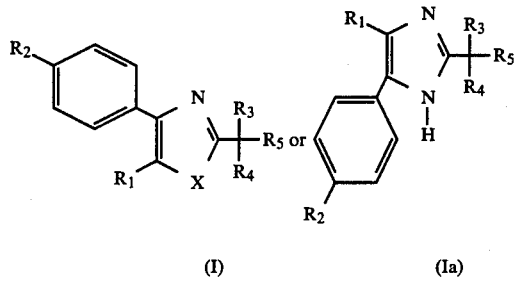

(I)  (Ia)

wherein

X is NH, S or O;

$R_1$ is a straight or branched chain alkyl of 1–7 carbon atoms, a straight or branched chain alkylene or alkyne of 2–7 carbon atoms, said alkyl, alkylene or alkyne optionally mono-, di- or tri-substituted with F, Cl or Br, cycloalkyl, cycloalkenyl, or cycloalkylalkyl of 3–7 carbon atoms, or

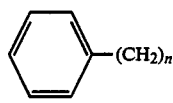

where n is 1 or 2;

$R_2$ is $C_1$–$C_2$ alkyl $S(O)_m$ where m is 0, 1 or 2, $C_1$–$C_2$ alkoxy, cyano, acetyl or $NO_2$;

$R_3$ and $R_4$ independently are $CF_3$, $CF_2H$, $CF_2Cl$, $CFCl_2$, $CF_3CF_2$ or $CF_3CF_2CF_2$;

$R_5$ is $OR_7$ or $NHR_7$ where $R_7$ is H, alkyl of 1–3 carbon atoms, or

where $R_8$ is alkyl of 1–3 carbon atoms, phenyl or phenyl monosubstituted with F, Cl, Br, $NO_2$, $CF_3$, $C_1$–$C_2$ alkyl, or $C_1$–$C_2$ alkoxy, with the proviso that when $R_5$ is $NHR_7$ then X is NH; or a pharmaceutically suitable salt thereof.

2. A compound of claim 1 wherein $R_5$ is other than $NHR_7$.

3. A compound of claim 1 wherein $R_1$ is alkyl of 1–4 carbon atoms.

4. A compound of claim 1 wherein $R_2$ is $C_1$–$C_2$ alkyl $S(O)_m$ where m is 0, 1 or 2.

5. A compound of claim 1 wherein $R_3$ and $R_4$ are $CF_3$.

6. A compound of claim 1 wherein $R_5$ is OH.

7. A compound of claim 1 wherein $R_1$ is alkyl of 1–4 carbon atoms, $R_2$ is $C_1$–$C_2$ alkyl $S(O)_m$ where m is 0, 1 or 2, $R_3$ and $R_4$ are $CF_3$, and $R_5$ is OH.

8. The compound of claim 1 which is 4-(1-methylethyl)-5-(4-methylsulfonylphenyl)-α,α-bis(trifluoromethyl)imidazole-2-methanol.

9. The compound of claim 1 which is 4-ethyl-5-(4-methylsulfonylphenyl)-α,α-bis(trifluoromethyl)imidazole-2-methanol.

10. The compound of claim 1 which is 4-(phenylmethyl)-5-(4-methylsulfonylphenyl)-α,α-bis(trifluoromethyl)imidazole-2-methanol.

11. The compound of claim 1 which is 4-cyclopentyl-5-(4-methylsulfonylphenyl)-α,α-bis(trifluoromethyl)imidazole-2-methanol.

12. The compound of claim 1 which is 4-cyclohexyl-5-(4-methylsulfonylphenyl)-α,α-bis(trifluoromethyl)imidazole-2-methanol.

13. The compound of claim 1 which is 5-(1-methylethyl)-4-(4-methylsulfonylphenyl)-α,α-bis(trifluoromethyl)thiazole-2-methanol.

14. The compound of claim 1 which is 5-ethyl-4-(4-methylsulfonylphenyl)-α,α-bis-(trifluoromethyl)-thiazole-2-methanol.

15. The compound of claim 1 which is 5-ethyl-4-(4-methylsulfonylphenyl)-α,α-bis(trifluoromethyl)oxazole-2-methanol.

16. A pharmaceutical composition consisting essentially of a suitable pharmaceutical carrier and an effective antihypertensive amount of a compound of claim 1.

17. A pharmaceutical composition consisting essentially of a suitable pharmaceutical carrier and an effective antihypertensive amount of a compound of claim 2.

18. A pharmaceutical composition consisting essentially of a suitable pharmaceutical carrier and an effective antihypertensive amount of a compound of claim 3.

19. A pharmaceutical composition consisting essentially of a suitable pharmaceutical carrier and an effective antihypertensive amount of a compound of claim 4.

20. A pharmaceutical composition consisting essentially of a suitable pharmaceutical carrier and an effective antihypertensive amount of a compound of claim 5.

21. A pharmaceutical composition consisting essentially of a suitable pharmaceutical carrier and an effective antihypertensive amount of a compound of claim 6.

22. A pharmaceutical composition consisting essentially of a suitable pharmaceutical carrier and an effective antihypertensive amount of a compound of claim 7.

23. A pharmaceutical composition consisting essentially of a suitable pharmaceutical carrier and an effective antihypertensive amount of the compound of claim 8.

24. A pharmaceutical composition consisting essentially of a suitable pharmaceutical carrier and an effective antihypertensive amount of the compound of claim 9.

25. A pharmaceutical composition consisting essentially of a suitable pharmaceutical carrier and an effective antihypertensive amount of the compound of claim 10.

26. A pharmaceutical composition consisting essentially of a suitable pharmaceutical carrier and an effective antihypertensive amount of the compound of claim 11.

27. A pharmaceutical composition consisting essentially of a suitable pharmaceutical carrier and an effective antihypertensive amount of the compound of claim 12.

28. A pharmaceutical composition consisting essentially of a suitable pharmaceutical carrier and an effective antihypertensive amount of the compound of claim 13.

29. A pharmaceutical composition consisting essentially of a suitable pharmaceutical carrier and an effective antihypertensive amount of the compound of claim 14.

30. A pharmaceutical composition consisting essentially of a suitable pharmaceutical carrier and an effective antihypertensive amount of the compound of claim 15.

31. A method of treating hypertension in a mammal comprising administering to the mammal an antihypertensive amount of a compound of claim 1.

32. A method of treating hypertension in a mammal comprising administering to the mammal an antihypertensive amount of a compound of claim 2.

33. A method of treating hypertension in a mammal comprising administering to the mammal an antihypertensive amount of a compound of claim 3.

34. A method of treating hypertension in a mammal comprising administering to the mammal an antihypertensive amount of a compound of claim 4.

35. A method of treating hypertension in a mammal comprising administering to the mammal an antihypertensive amount of a compound of claim 5.

36. A method of treating hypertension in a mammal comprising administering to the mammal an antihypertensive amount of a compound of claim 6.

37. A method of treating hypertension in a mammal comprising administering to the mammal an antihypertensive amount of a compound of claim 7.

38. A method of treating hypertension in a mammal comprising administering to the mammal an antihypertensive amount of the compound of claim 8.

39. A method of treating hypertension in a mammal comprising administering to the mammal an antihypertensive amount of the compound of claim 9.

40. A method of treating hypertension in a mammal comprising administering to the mammal an antihypertensive amount of the compound of claim 10.

41. A method of treating hypertension in a mammal comprising administering to the mammal an antihypertensive amount of the compound of claim 11.

42. A method of treating hypertension in a mammal comprising administering to the mammal an antihypertensive amount of the compound of claim 12.

43. A method of treating hypertension in a mammal comprising administering to the mammal an antihypertensive amount of the compound of claim 13.

44. A method of treating hypertension in a mammal comprising administering to the mammal an antihypertensive amount of the compound of claim 14.

45. A method of treating hypertension in a mammal comprising administering to the mammal an antihypertensive amount of the compound of claim 15.

* * * * *